US009460494B2

(12) United States Patent
Krol et al.

(10) Patent No.: US 9,460,494 B2
(45) Date of Patent: Oct. 4, 2016

(54) METHODS AND SYSTEMS FOR INVERSE PROBLEM RECONSTRUCTION AND APPLICATION TO ECT RECONSTRUCTION

(71) Applicants: Andrzej Krol, Syracuse, NY (US); Yuesheng Xu, Syracuse, NY (US); Si Li, Syracuse, NY (US); Lixin Shen, Syracuse, NY (US)

(72) Inventors: Andrzej Krol, Syracuse, NY (US); Yuesheng Xu, Syracuse, NY (US); Si Li, Syracuse, NY (US); Lixin Shen, Syracuse, NY (US)

(73) Assignee: The Research Foundation for the State University of New York, Syracuse, NY (US)

( * ) Notice: Subject to any disclaimer, the term of this patent is extended or adjusted under 35 U.S.C. 154(b) by 21 days.

(21) Appl. No.: 14/374,158

(22) PCT Filed: Feb. 1, 2013

(86) PCT No.: PCT/US2013/024414
§ 371 (c)(1),
(2) Date: Jul. 23, 2014

(87) PCT Pub. No.: WO2013/116701
PCT Pub. Date: Aug. 8, 2013

(65) Prior Publication Data
US 2015/0145885 A1    May 28, 2015

Related U.S. Application Data

(60) Provisional application No. 61/594,765, filed on Feb. 3, 2012.

(51) Int. Cl.
| G06T 5/00 | (2006.01) |
| G06T 11/00 | (2006.01) |
| A61B 6/03 | (2006.01) |
| G06K 9/52 | (2006.01) |

(52) U.S. Cl.
CPC ............... *G06T 5/002* (2013.01); *A61B 6/03* (2013.01); *G06K 9/522* (2013.01); *G06T 11/006* (2013.01); *G06T 2207/10072* (2013.01); *G06T 2211/424* (2013.01)

(58) Field of Classification Search
CPC ............... G06T 11/003; G06T 2207/10072; G06T 2211/40; G06T 2211/424
See application file for complete search history.

(56) References Cited

U.S. PATENT DOCUMENTS

| 7,109,489 B2 | 9/2006 | Shwartz et al. |
| 9,020,230 B2 * | 4/2015 | Yu ............ G06T 11/006 382/131 |

(Continued)

FOREIGN PATENT DOCUMENTS

WO    2011100723 A2    8/2011

OTHER PUBLICATIONS

International Search Report dated May 15, 2013 for PCT/US12/24414.

(Continued)

*Primary Examiner* — Antonio A Caschera
(74) *Attorney, Agent, or Firm* — Burns & Levinson LLP; Orlando Lopez

(57) ABSTRACT

Methods and systems for obtaining a reconstruction of an object, the reconstruction of the object comprising an inverse problems. Expressing the reconstruction of the object as a optimization problem with total variation regularization, and obtaining the reconstruction of the object from convergence of the iterations, an object being an input/representation of input to a system, the system providing output data resulting from the input, the object being reconstructed from the output data obtained from interaction of the object with the system.

23 Claims, 10 Drawing Sheets

(56) References Cited

U.S. PATENT DOCUMENTS

| | | | |
|---|---|---|---|
| 9,140,770 B2 * | 9/2015 | Odille | G01R 33/5611 |
| 2006/0067461 A1 | 3/2006 | Yin et al. | |
| 2007/0242796 A1 | 10/2007 | Vengrinovich et al. | |
| 2009/0253898 A1 * | 10/2009 | Engl | G06F 19/16 |
| | | | 530/350 |
| 2010/0284596 A1 | 11/2010 | Miao et al. | |
| 2011/0044546 A1 | 2/2011 | Pan et al. | |
| 2011/0105880 A1 | 5/2011 | Yu et al. | |
| 2015/0146949 A1 * | 5/2015 | Pan | G06T 11/006 |
| | | | 382/130 |

OTHER PUBLICATIONS

Bonettini, S. et al. An alternating extragradient method for total variation based image restoration from Poissono data. Inverse Problems 27(9) (Sep. 2011): 1-28.

Bostan, E. et al. Reconstruction of Biomedical Images and Sparse Stochastic Modeling. 9th IEEE International Symposium on Biomedical Imaging (ISBI) (May 2-5, 2012): 880-883.

Chambolle, A. An Algorithm for Total Variation Minimization and Applications. Journal of Mathematical Imaging and Vision (Jan. 2004) 20(1-2): 89-97.

Clinthorne, N.H. et al. Preconditioning Methods for improved Convergence Rates in Iterative Reconstructions. IEEE Transactions on Medical Imaging 12(1) (Mar. 1993): 78-83.

Grote, M.J. et al. Parallel Preconditioning with Sparse Approximate Inverses. SIAM J. Sci. Comput. 18(3) (May 1997): 838-853.

Lange, K. et al. A Theoretical Study of Some Maximum Likelihood Algorithms for Emission and Transmission Tomography. IEEE Transactions on Medical Imaging 6(2) (Jun. 1987): 106-114.

Mumcuoglu, E.U. et al. Fast Gradient-Based Methods for Bayesian Reconstruction of Transmission and Emission PET Images. IEEE Transactions on Medical Imaging 13(4) (Dec. 1994): 687-701.

* cited by examiner

| tol / Algorithm | $10^{-1}$ | $10^{-2}$ | $10^{-3}$ | $10^{-4}$ | $10^{-5}$ | $10^{-6}$ | $10^{-7}$ |
|---|---|---|---|---|---|---|---|
| Algorithm 1 ($S = 1$) | (5.4, 2) | (70.2, 27) | (250.9, 99) | (1359.6, 525) | (4300.9, 1653) | (10 241.8, 3940) | (-, -) |
| Algorithm 1 ($S = T$) | (5.4, 2) | (57.5, 23) | (210.5, 85) | (1088.5, 445) | (3204.9, 1301) | (7383.4, 3000) | (-, -) |
| Algorithm 2 | (12.6, 5) | (35.0, 14) | (109.6, 44) | (291.1, 117) | (768.6, 309) | (1915.6, 770) | (5435.0, 2109) |
| Algorithm 3 | (12.3, 5) | (34.8, 14) | (109.6, 44) | (305.7, 123) | (759.5, 307) | (1464.3, 592) | (3954.8, 1599) |
| P-PD Algorithm | (6.6, 2) | (75.9, 23) | (292.7, 89) | (1569.1, 479) | (4357.6, 1331) | (9885.1, 3024) | (-, -) |

Fig. 5c

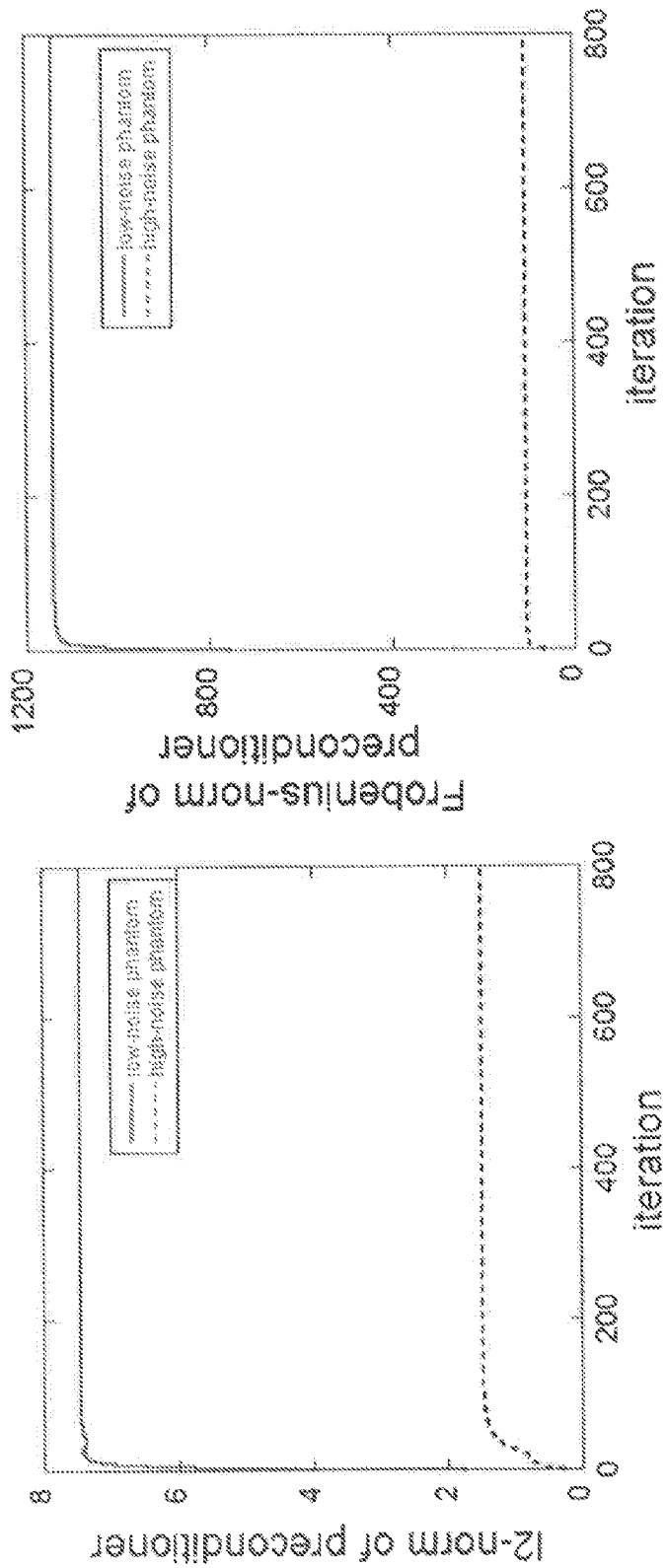

METHODS AND SYSTEMS FOR INVERSE PROBLEM RECONSTRUCTION AND APPLICATION TO ECT RECONSTRUCTION

CROSS-REFERENCE TO RELATED APPLICATIONS

This application is a U.S. national stage application under 35 U.S.C. 371 of co-pending International Application No. PCT/US2013/024414 filed on Feb. 1, 2013 and entitled METHODS AND SYSTEMS FOR INVERSE PROBLEM RECONSTRUCTION AND APPLICATION TO ECT RECONSTRUCTION, which in turn claims priority to and benefit of U.S. Provisional Patent Application No. 61/594,765, filed on Feb. 3, 2012, which is incorporated by reference herein in its entirety for all purposes.

BACKGROUND

These teachings relate generally to Reconstruction of images, and, more particularly, to reconstruction of images involving an inverse problem.

One exemplary instance of the reconstruction of images is reconstruction of ECT images.

Emission computed tomography (ECT) is an important scientific and medical imaging technique that can be divided into two branches: positron emission tomography (PET) and single-photon emission computed tomography (SPECT). Clinical applications of ECT include the detection, staging and monitoring response to therapy of cancer, detection and risk stratification of cardiovascular diseases, mapping of regional blood flow in the brain, bone scans, pulmonary ventilation/perfusion scans, renal scans and many others. In the nuclear medicine ECT examination a patient is administered a radiotracer that has adequate specificity and sensitivity for a given clinical detection task. The SPECT or PET camera counts photons that were recorded in discrete detector bins at various spatial locations, typically distributed 360 degrees about the patient. The reconstruction process attempts to estimate mean radiotracer activity distribution ($f$) inside the body of a patient.

There is a great need to reduce radiation dose to the patients undergoing ECT examinations. This could be accomplished by lowering the total amount of activity in the radiotracer administered. However, lowering the total amount of activity in the radiotracer administered would lead to very high Poisson noise in the raw ECT data. In turn, such very noisy data if treated by the conventional ECT reconstruction techniques, e.g. FBP, MLEM, MAP-EM, OSL, OSEM, or RBBI, would lead to very noisy and clinically unacceptable reconstructed images.

There is a need for ECT reconstruction techniques that can provide good quality ECT reconstructions from low-dose ECT examinations.

There is also a need for image reconstruction techniques that can provide good quality image reconstructions under high noise conditions.

BRIEF SUMMARY

In one or more embodiments, the method of these teachings for obtaining a reconstruction of an object, the reconstruction of the object comprising an inverse problems, includes expressing the reconstruction of the object as a optimization problem with total variation regularization, and obtaining the reconstruction of the object from convergence of the iterations, an object being an input/representation of input to a system, the system providing output data resulting from the input, the object being reconstructed from the output data obtained from interaction of the object with the system.

In one instance, the projections are expressed using proximity operators. In another instance, the method also includes using a preconditioner in one of the fixed point equations using projections in order to improve convergence while not substantially affecting result of the convergence.

In one instance, the present teachings provide methods for improved emission computed tomography (ECT) and, more specifically, methods for improved reconstructions in single photon computed tomography (SPECT) and positron emission tomography (PET). Embodiments provide a method and a system for reconstructing an image from projection data provided by a single photon emission computed tomography or positron emission tomography scanner comprising reconstructing of the image with lower noise and/or at lower radiation dose, wherein the reconstructing comprises performing a reconstruction method that yields an exact and stable reconstruction.

Other embodiments of the method and system and computer program product of these teachings are also disclosed.

In one embodiment, the preconditioned alternating projection algorithm (PAPA) of these teachings can be applied to solving the Maximum A Posteriori (MAP) ECT reconstruction problem. The algorithm of these teachings enjoys nice theoretical convergence results in the case that the preconditioner is fixed. Dynamic and semi-dynamic Expectation Maximization (EM)-preconditioners for the PAPA are used to accelerate the convergence of the original iterative scheme. Numerical experiments demonstrate that the EM-preconditioner, as used in the PAPA of these teachings, converges fast to a fixed preconditioning matrix, which in turn confirms the applicability of the convergence result to the practical situation. Since the Total Variation (TV)-based penalty function can well preserve the edges and details of the reconstructed object, example with TV regularization are presented. Based on the numerical experiments performed, it is shown that the alternating projection algorithm of these teachings with the EM-preconditioner significantly outperforms the conventional EM-TV algorithm in all aspects including the convergence speed, the noise in the reconstructed image and the image quality. It also outperforms the recently developed algorithm—the nested EM-TV—in the convergence speed while having a comparable image quality.

The alternating projection algorithm of these teachings with dynamic or semi-dynamic EM-preconditioner can allow significant reduction in the radiation dose to the patients imaged using ECT by providing the same CNR for hot and cold lesions as the conventional EM-TV, but with the total administered radiotracer activity two to six times lower than presently used in ECT examinations reconstructed using the conventional EM-TV.

For a better understanding of the present teachings, together with other and further needs thereof, reference is made to the accompanying drawings and detailed description and its scope will be pointed out in the appended claims.

BRIEF DESCRIPTION OF THE DRAWINGS

FIG. 5c is a table of CPU times (process times);

FIGS. 6a, 6b show Curves of (a) $\ell^2$-norm and (b) Frobenius norm of the preconditioner versus iteration numbers for low-noise and high-noise phantoms;

DETAILED DESCRIPTION

Figure 1:
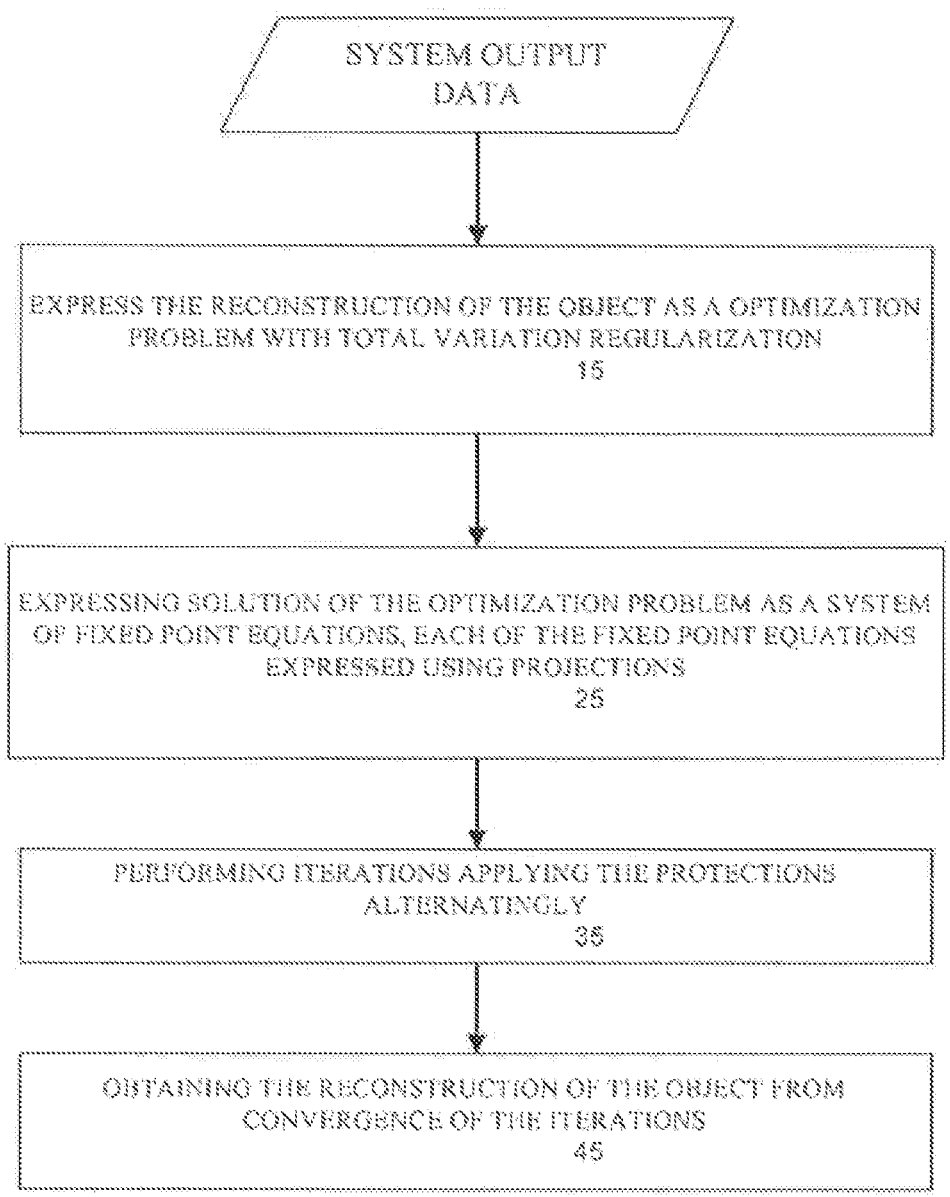
FIG. 1 is a schematic flow diagram representation of one embodiment of the method of these teachings.

The following detailed description presents the currently contemplated modes of carrying out the invention. The description is not to be taken in a limiting sense, but is made merely for the purpose of illustrating the general principles of the invention, since the scope of the invention is best defined by the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

Methods and systems for Reconstruction of images, and, more particularly, to reconstruction of images involving an inverse problem, including the reconstruction of ECT images, are disclosed hereinbelow.

In order to facilitate in the description of the method and system of these teachings, the following definitions are provided.

A "maximum a posteriori probability (MAP) estimate," is a Bayesian statistic expression obtained by maximizing the conditional a posteriori probability p(f|g), the probability that f occurs when g is observed, which is used to obtain an estimate of an unobserved quantity on the basis of empirical data.

"Total Variation regularization" is a process, having applications in noise removal, that is based on the principle that signals with excessive and possibly spurious detail have high total variation, that is, the integral of the absolute gradient of the signal is high.

In some instances, in ECT reconstruction for example, the poorly conditioned nature of a system response matrix can cause amplification of the errors in the projection data resulting from Poisson counting noise. In order to reduce this sensitivity to noise, total variation regularization adds a stabilizing term as a term to the objective functional in order to penalize solutions inconsistent with convergence behavior:

The "◯" mathematical symbol, as used herein, represents the function composition symbol which can be defined by example as $f \circ g$ is the function, such that $(f \circ g)(x)=f(g(x))$.

Hereinbelow, the same notation '1' is used to represent both the scalar number 1 and the vector with all components equal to 1. They can be distinguished by the context of their use.

For any vectors x and y in $R^k$, the following are defined: $\langle \bullet, \bullet \rangle$ is the inner product and $\|\bullet\|$ is the $l^2$ norm in an Euclidean space and $\|\bullet\|_\infty$ is the $l^\infty$ norm.

The "projection of vector x" onto a convex, closed set C is defined as $$proj_C(x) := \underset{u \in \mathbb{R}^d}{\mathrm{argmin}} \frac{1}{2}\|u-x\|_2^2 + \chi_C(u),$$

where $$\chi_C(u) = \begin{cases} 0 & u \in C; \\ +\infty & \text{otherwise} \end{cases},$$

is the indicator function of set C. Particularly, when C is chosen as $C^+:=\{u \in R^d | u_i \geq 0, i=1, \ldots, d\}$, the projection operator can be expressed as:

$$proj_{C+}(x)=\max\{x,0\},$$

where $\max\{x, 0\}$ is the vector with its i-th component zero if xi<0 and xi otherwise.

Let $\psi$ be a real-valued convex function on Rd. The "proximity operator of $\psi$" is defined for x∈Rd by $$prox_\psi x := \mathrm{argmin}\left\{\frac{1}{2}\|u-x\|_2^2 + \psi(u) : u \in \mathbb{R}^d\right\}.$$

Note that proximity operator is a natural extension of projection operator, whereby the indicator function is replaced by an arbitrary convex function on finite-dimensional space. Proximity operators generalize Euclidean projectors: consider the case
$\phi=i_C$, where C∈$R^P$ is a convex set and $i_C$ enotes its indicator (i.e.

$$\varphi(u) := \begin{cases} 0 & \text{if } u \in C \\ +\infty & \text{otherwise} \end{cases}.$$

Then, prox' is the Euclidean projector onto C.

In one or more embodiments, as shown in FIG. 1, the method of these teachings for obtaining a reconstruction of an object, the reconstruction of the object comprising an inverse problems, includes expressing the reconstruction of the object as a optimization problem with total variation regularization (step 15, FIG. 1), expressing solution of the optimization problem as a system of fixed point equations, each of the fixed point equations expressed using projections (step 25, FIG. 1), performing iterations applying the protections alternatingly (step 35, FIG. 1) and obtaining the reconstruction of the object from convergence of the iterations (step 45, FIG. 1), an object being an input/representation of input to a system, the system providing output data resulting from the input, the object being reconstructed from the output data obtained from interaction of the object with the system.

In one instance, at least some of the projections are expressed using proximity operators. In another instance, the reconstruction of the object is expressed as $$\min\{<Af,1>-<\ln(Af+\gamma),g>+\lambda(\phi \circ B)(f):f \in Rd\}.$$

where g is the output data resulting from the input,
ƒ is the object,
A is the operator representing the system,
γ is the background noise,
λ is a regularization parameter, and
(φ∘B)(ƒ) is a total variation regularization expression;
and the fixed point equations are $$b=(l-\text{prox}_{\mu^{-1}\phi})(b+\sigma \nabla_b H(f,b)),$$

$$f=\text{prox}_\gamma(f-\tau S \nabla_f H(f,b)).$$

where l is the identity matrix or operator,
prox is the proximity
operator, ∇ is the gradient operator with respect to the subscripted variable, $$H=<Af,1>-<\ln(Af+\gamma),g>+\lambda(\phi \circ B)(f):f \in Rd$$

λ, β and μ are positive numbers, $$\tau := \frac{\beta}{\lambda}, \sigma := \frac{1}{\lambda\mu}$$

and S is a predetermined matrix including the identity matrix.

In yet another instance, a preconditioner is used in one of the fixed point equations using projections in order to improve convergence while not substantially affecting result of the convergence. In one embodiment of the above equation, S is a preconditioner matrix. In another embodiment, the preconditioner in one iteration is different from the preconditioner in a subsequent iteration.

In a number of detailed embodiments, the object is an image from emission computed tomography (ECT), output data is scanner projection data; the system being expressed as:

$$g=Af+\gamma$$

where g are expected photon counts, A is a system matrix,
ƒ is a expected radiotracer distribution, γ is background photon count.

In one instance of the ECT embodiments, in the equation provided herein above, S is a preconditioner matrix given by $$\text{Diag}\left(\frac{f^{(k)}}{A^T 1}\right)$$

where diag indicates a diagonal matrix, $A^T$ is the transpose of the system matrix, 1 is the unitary matrix.

Figure 2:
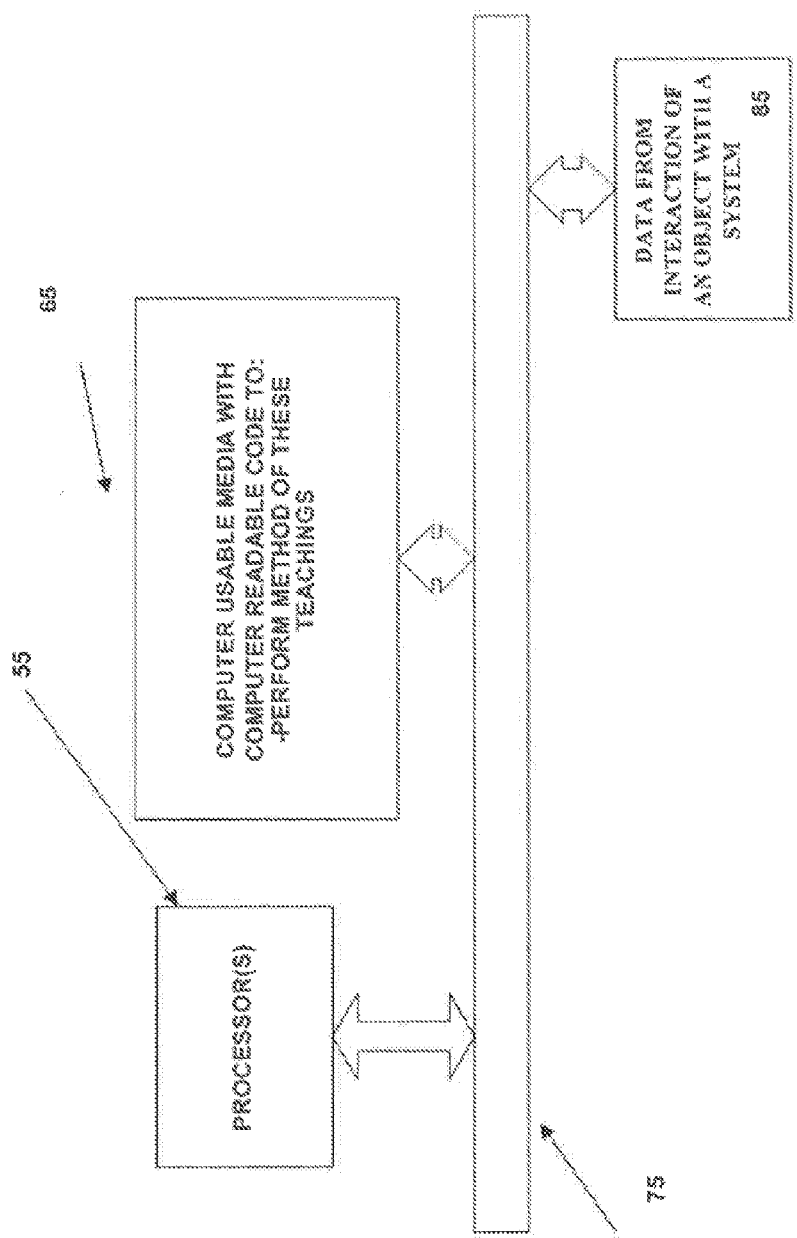
FIG. 2 is a schematic block diagram representation of one embodiment of the system of these teachings.

In one or more embodiments, as shown in FIG. 2, the system of these teachings includes one or more processors (55, FIG. 2) and one or more computer usable media (65, FIG. 2) having computer readable code embodied therein, the computer readable code causing said at least one processor to receive data (85, FIG. 2) from interaction of an object with a system, express the reconstruction of the object as a optimization problem with total variation regularization, express solution of the optimization problem as a system of fixed point equations, each of the fixed point equations expressed using projections, perform iterations applying the protections alternatingly and obtain the reconstruction of the object from convergence of the iterations, where the object is an input to a system, the system provides output data resulting from the input, the object is reconstructed from the output data obtained from interaction of the object with the system. In the embodiment shown in FIG. 2, the one or more processors 55, the computer readable media 65 and the interface to receive data 85 are operatively connected by an interconnection component 75 (a computer bus in one embodiment).

In one instance of the system of these teachings, at least some of the projections are expressed using proximity operators. In another instance, the reconstruction of the object is expressed as $$\min\{<Af,1>-<\ln(Af+\gamma),g>+\lambda(\phi \circ B)(f):f \in Rd\}.$$

where g is the output data resulting from the input,
ƒ is the object,
A is the operator representing the system,
γ is the background noise,
λ is a regularization parameter, and
(φ∘B)(ƒ) is a total variation regularization expression;
and the fixed point equations are $$b=(l-\text{prox}_{\mu^{-1}\phi})(b+\sigma \nabla_b H(f,b)),$$

$$f=\text{prox}_\gamma(f-\tau S \nabla_f H(f, b)).$$

where l is the identity matrix or operator,
prox is the proximity
operator, ∇ is the gradient operator with respect to the subscripted variable, $$H=<Af,1>-<\ln(Af+\gamma),g>+\lambda(\phi \circ B)(f):f \in Rd$$

λ, β and μ are positive numbers, $$\tau := \frac{\beta}{\lambda}, \sigma := \frac{1}{\lambda\mu}$$

and S is a predetermined matrix including the identity matrix.

In yet another instance of the system of these teachings, a preconditioner is used in one of the fixed point equations using projections in order to improve convergence while not substantially affecting result of the convergence. In one embodiment of the above equation, S is a preconditioner matrix. In another embodiment, the preconditioner in one iteration is different from the preconditioner in a subsequent iteration.

In order to further elucidate these teachings, exemplary embodiments are presented below. It should be noted that these teachings are not limited only to the exemplary embodiments.

Since, in some of the exemplary embodiment, the methods and systems of these teachings are applied to ECT reconstruction, a background discussion of ECT reconstruction is presented below.

Emission computed tomography (ECT) i.e. single photon emission computed tomography or positron emission tomography scanners projection could be modeled by the following equation:

$$g = Af + \gamma$$

where g are expected photon counts, A is the system matrix, $f$ is the expected radiotracer distribution, $\gamma$ is background.

The reconstruction process attempts to estimate mean radiotracer activity distribution ($f$) inside the body of a patient. It is governed by molecular and/or functional processes and allows clinicians to arrive at diagnoses. The relationship between the continuous mean radiotracer activity distribution $f$ and the discrete random vector g recorded by the detector can be described by the following integral equations:

$$\hat{g}_i = \text{Poisson}(\int_{\Omega} h_i(x) f(x) dx) + \text{Poisson}(\gamma), i=1,2,\ldots,m, \quad (1)$$

where Poisson(a) denotes a Poisson random variable with Poisson parameter a, C2 is the image space, $h_i(x)$ is probability that nuclear decay at location x is recorded by i-th detector unit, $\gamma$ is the expected number of "background" counts (e.g. due to cosmic rays or radon) recorded by each detector bin in time interval $[t_1, t_2]$, and the emission rate density $f(x)$ is defined by $$f(x) = \mu_N \int_{t_1}^{t_2} \frac{1}{\mu_T} e^{-\frac{t}{\mu_T}} p_x(t) dt. \quad (2)$$

The number of administrated radioatoms has a Poisson distribution with mean AN. Radio-active decay of tracer atoms is described by an exponential distribution with mean $A_T = T_{1½}/\ln 2$, where $T_{1½}$ is the specific radiotracer isotope decay half-life The $p_x(t)$ is the probability density function describing radiotracer distribution at time t.

The term g in Equation (1) is the sum of two Poisson random vectors. By calculating the expectations of both sides of (1), we obtain the mean vector g for random vector g as follows:

$$\bar{g}_i = A_i f + \gamma, i=1,2,3 \ldots m, \quad (3)$$

where $A_i$ represents the integral operator in (1).

In order to numerically solve the equations (3), a d-dimensional base is introduced to represent the voxel-wise constant approximation of the continuous mean activity distribution $f$. The three-dimensional image space $\Omega$ is divided into d isometric cubes (voxels). Corresponding to each cube $\Omega j$, $j=1, 2, \ldots, d$ the basis function is defined as $$\psi_j(x) = \begin{cases} 1 & x \in \Omega_j \\ 0 & \text{otherwise} \end{cases} \quad (4)$$

After approximating $f$ by linear combination $\Sigma f_j \psi_j$ we obtain discrete representations for equations (3):

$$\bar{g}_j = \Sigma a_{ij} f_j + \gamma \quad (5)$$

Where $a_{ij} = \int_{\Omega j} h_i(x) dx$ are entries of the system matrix A of the emission imaging system.

The objective is to accurately (i.e. with lowest bias) estimate (reconstruct) the expected activity distribution E($f$) while suppressing the noise (variance) and preserving the spatial resolution in the estimation. The well-known maximum likelihood (ML) estimation approach is used when a priori information about the emission rate density function $f$ is not sufficiently well known. In contrast, Bayesian model assumes that the unobservable parameter $f$ is a random variable statistically related to the observed data random variable g through a known set of probability distribution functions. The maximum a posteriori probability (MAP) estimate has proven its usefulness in ECT when the observed data are very noisy or incomplete.

A reconstruction method of these teachings includes maximum a posteriori reconstructing an image from ECT data by minimizing the total variation while minimizing the discrepancy between the modeled projection data and the actual projection data defined as follows:

$$\min_{f \in C+} \{<Af,e> - <\ln(Af+\gamma),g> + \lambda \|f\|_{TV}\} \quad (6)$$

where $\|f\|_{TV} = (\phi \circ B)(f): f \in R_+^d$ where $\lambda$ is a regularization hyperparameter, $e \in R^m$ denotes a unit vector, $\gamma \in R^m$ denotes a vector with all components equal to $\gamma$, $C+ = \{u \in R^d | u_i \leq 0, i=1, \ldots, d\}$ is a closed convex set, $\|f\|_{TV}$ is the total variation norm.

Although the variational problem (6) is derived in the specific context of the ECT image reconstruction, in this paper, the problem stated by equation (6) can be used to represent other inverse problems. Hereinbelow, A is a matrix in $R^{m \times d}$, g is a given vector in $R^m$, $\gamma$ is a positive vector in $R^m$, $\lambda$ is a positive number, $\phi$ is a convex nonnegative function on $R^n$ and B is an n×d matrix. The ECT image reconstruction model is a special case of the model defined by equation (6) when $\phi \circ B$ is chosen as the TV semi-norm.

In order to further elucidate these teachings, the following definitions are useful:

The indicator function, $i_C$, of a closed convex set C in H is defined as $$i_C(u) := \begin{cases} 0 & \text{if } u \in C \\ +\infty & \text{otherwise} \end{cases}$$

when the set C is $R_d+$, the following can be defined $$\Gamma = i_{Rd+},$$

Then if f is a solution of the minimization problem, there exists a b which is a solution of the following coupled equations $$b = (l - \text{prox}_{\mu^{-1}\phi})(b + \sigma \nabla_b H(f,b)),$$

$$f = \text{prox}_\gamma (f - \tau S \nabla_f H(f,b)).$$

where l is the identity matrix or operator, prox is the proximity operator, $\nabla$ is the gradient operator with respect to the subscripted variable, $$H = <Af,1> - <\ln(Af+\gamma),g> + \lambda(\phi \circ B)(f): f \in Rd$$

$\lambda$, $\beta$ and $\mu$ are positive numbers, $$\tau := \frac{\beta}{\lambda}, \sigma := \frac{1}{\lambda \mu}$$

and S is a predetermined matrix including the identity matrix.

Other characterizations of the coupled equation are possible, for example $$b = (I - \text{prox}_{\mu^{-1}\phi})(b + \sigma \nabla_b H(f,b)),$$

$$f = \text{prox}_\gamma(f - \tau S \nabla_1 H(f,b)).$$

In iterations, the solution to the coupled equations can be expressed as $$h^{(k)} := \text{prox}_\gamma(f(k) - \tau S \nabla_f H(f^{(k)}, b^{(k)})).$$

$$b^{(k+1)}(I - \text{prox}_{\mu^{-1}\phi})(b^{(k)} + \sigma \nabla_b H(h^{(k)}, b^{(k)})),$$

$$f^{(k+1)} = \text{prox}_\gamma(f^{(k)} - \tau S \nabla_f H(f^{(k)}, b^{(k+1)}))$$

It can also be shown that the operators $(I - \text{prox}_{\mu^{-1}\phi})$ and proxy are projections.

Figure 3:
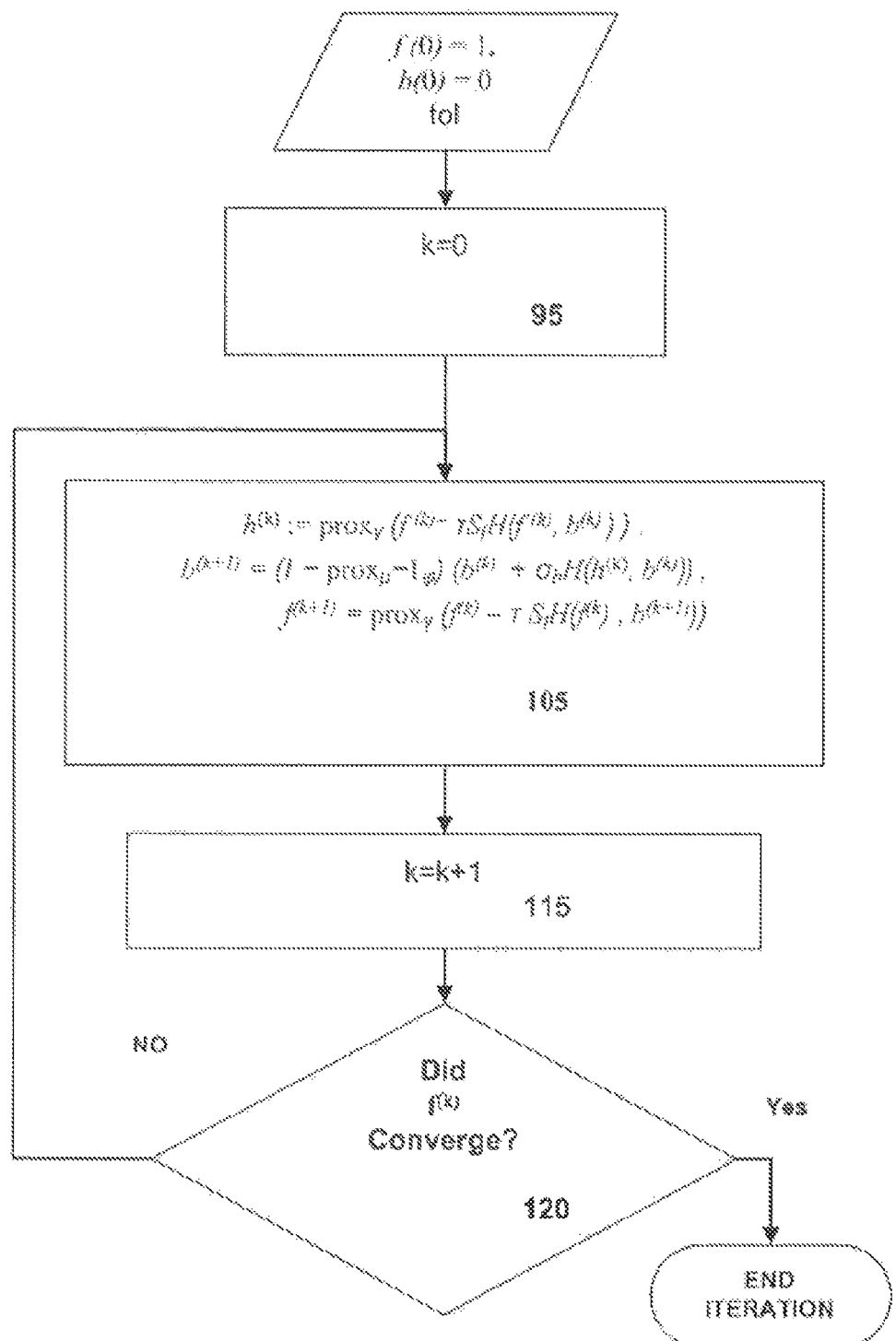
FIG. 3 is a schematic flow diagram representation of one embodiment of the iteration step in one embodiment of the method of these teachings.

FIG. 3 shows a flowchart of an embodiment of the iteration step in the method of these teachings where the coupled equations shown hereinabove are used. Referring to FIG. 3, in the embodiment shown therein, initialization values are provided (tol is the tolerance amount for determining convergence) and the index is set to zero (step 95, FIG. 3). The expression for the iteration of the coupled equations provided herein above is used to obtain their values at the next index number (step 105, FIG. 3). The index is then increased by one (step 115, FIG. 3). It should be noted that in some embodiments steps 105 to 115 are repeated a number of times before convergence is checked. Convergence or lack of convergence is then determined (step 120, FIG. 3) using $$\frac{\|f^{(k)} - f^{(k+1)}\|}{\|f^{(k+1)}\|} \leq tol.$$

If the above inequality is not satisfied, the iteration continues.

A more compact manner representation can be obtained by defining an operator $Q_h^r : R^n \to R^n$, with $$Q_h^0 = I \text{ and } Q_h := (I - \text{prox}_{\mu - 1\phi}(\bullet + Bh))$$

$Q_h^r$ being defined recursively by $Q_h^r := Q_h \circ Q_h^{r-1}$
where $\phi$ is a convex nonnegative function in $R^n$
and B is an n×d matrix.

Using the more compact representation, the solution of the minimization problem of equation (6) can be shown to be given by the solution of the coupled equations $$b = Q_h^r(b)$$

$$f = \text{prox}_\gamma(f - \tau S \nabla_f H(f,b))$$

In order to further elucidate the convergence consideration of the algorithm of these teachings, the notion of the weighted norm is introduced below. For a symmetric and positive-definite matrix T: H→H, the weighted inner product is defined as $$\langle x, y \rangle_T := \langle T^{-1} x, y \rangle \quad x, y \in H$$

and the weighted norm is defined as
$$\|x\|_T := \sqrt{\langle x, x \rangle_T}$$

Convergence of the solution of the minimization problem equation (6), which is the same as convergence of the solution of the coupled equations, can be defined as $$\frac{\|f^{(k)} - f^{(k+1)}\|_S}{\|f^{(k+1)}\|_S} < \epsilon$$

for some predetermined small E, the expression also applying when S=I. (Mathematical proofs for the above embodiments and convergence thereof can be found in A Krol et al, Inverse Problems 28 (2012) and in U.S. Provisional Application Ser. No. 61/594,765, filed Feb. 3, 2012, entitled ECT RECONSTRUCTION, which are incorporated by reference herein in its entirety and for all purposes.)

It should be noted that the above algorithms could also be expressed in terms of the Kullbach-Leibler divergence, which is the sum of the negative log-likelihood of observed emission data conditional on radiotracer distribution. (The Kullbach-Leibler divergence is in general terms a non-symmetric measure of the difference between two probability distributions P and Q.) In the exemplary embodiments disclosed hereinbelow, the preconditioned alternating projection algorithms (PAPA) disclosed hereinabove are applied to the MAP ECT reconstruction by specifying the function $\phi$, the matrices B and the preconditioning matrix S). In particular, explicit formulas are presented for the proximity operators for the two special convex functions involved in the algorithm. The importance of the inner iteration for efficient computation in the context of MAP ECT reconstruction is pointed out. Finally, the differences and advantages of algorithm of these teachings over those of several existing algorithms for the Poisson-TV model are presented.

First, explicit expressions of $\phi$ and B are presented according to the definition of the total variation (TV). The concrete of $\phi$ and B depend on how 3D images are vectorized. A 3D image is assembled by a stack of 2D images. For exposition, an image is considered to have a size of p xp xq. The image is treated as a vector in R in such a way that the ijkth voxel of the image, where i, j$\in N_p$ and k$\in N_q$, corresponds to the $(i+(j-1)p+(k-1)p^2)$th element of the vector in $R^{p^2 q}$. In the current section, we set $d := p^2 q$. To define the matrix B, an a×a difference matrix $D_a$ is defined by $$\begin{bmatrix} 0 & & & \\ -1 & 1 & & \\ & \ddots & \ddots & \\ & & -1 & 1 \end{bmatrix}$$

In terms of the notion of the matrix Kronecker product $\otimes$, the 3d×d matrix B is defined by $$\begin{bmatrix} I_q \otimes I_p \otimes D_p \\ I_q \otimes D_p \otimes I_p \\ D_q \otimes I_p \otimes I_p \end{bmatrix}$$

(The Kronecker product, denoted by $\otimes$, is an operation on two matrices of arbitrary size resulting in a block matrix; Kronecker product should not be confused with the usual matrix multiplication.)

The convex function $\phi: R^{3d} \to R$ is defined at $z \in R^{3d}$ as $$\varphi(z) := \sum_{i=1}^{d} \|[z_i, d_{d+i}, z_{2d+i}]^T\|$$

The isotropic TV of a vector $f$ is then expressed as $\phi(Bf)$.

Execution of the iterative scheme disclosed hereinabove requires the availability of explicit formulas for the proximity operators of functions $\phi$ defined hereinabove and the indicator function $\wp := i_{R_+^d}$. For a positive number $\mu$ and a vector $z \in R^{3d}$, the components of the vector $$y := \text{prox}_{\mu^{-1}\phi}(z)$$

can be computed by using the formula $$[y_i, y_{d+i}, y_{2d+i}]^T = \max\left\{\|[z_i, z_{d+i}, z_{2d+i}]^T\| - \frac{1}{\mu}, 0\right\} \frac{[z_i, z_{d+i}, z_{2d+i}]^T}{\|[z_i, z_{d+i}, z_{2d+i}]^T\|}$$

With the above formula, for any positive integer r and a vector $h \in R^d$, the operator $Q^Y_h$ defined hereinabove can be explicitly computed. The proximity operator of the indicator function Y (the projection operator onto the first octant $R^d$) also has an explicit expression. That is, for $x \in R^d$, $(\text{prox}_\phi(x))i = \max[x_i, 0]$, $i \in Nd$.

Thus, both $\text{prox}_{\mu^{-1}\phi}$ and $\text{prox}_\phi$ have closed forms in the current context. These closed forms are convenient for numerical evaluation of the proximity operators of the two specific functions in the sense that no further optimization problems are required to solve. These specific examples can be evaluated numerically within the machine precision, while, in general, computing the proximity operator of a convex function requires solving an optimization problem by its definition. Even in the situation when close forms of the proximity operators are available, some round-off errors may be introduced during computation. In such a case, stability considerations have to be taken into account when computing the proximity operator.

Based on the disclosure herein above, the following algorithm (algorithm 1 of these teachings) can be used for the MAP ECT reconstruction.

Algorithm 1: (Alternating projection algorithm for MAP ECT reconstruction with a fixed matrix S)
Preparation: $\nabla fH$, $\nabla bH$ and $\tau$ are defined hereinabove respectively. The parameter r is a positive integer.
Initialization: $f(0)=1$, $b^{(0)}=0$.
repeat
    Step 1: $h^{(k)} \leftarrow \text{prox}_Y(f^{(k)} - \tau S^{(k)} \nabla_f H(f^{(k)}, b^{(k)}))$
    Step 2: $b(k+1) \leftarrow Q^Y_{h(k)}(b(k))$
    Step 3: $f(k+1) \leftarrow \text{prox}Y(f^{(k)} - \tau S^{(k)} \nabla_f H(f^{(k)}, b^{(k+1)}))$
until 'convergence'

The parameter r in algorithm 1 is the iteration number for the inner iteration. When r is chosen to be 1, three steps in algorithm 1 correspond to the three equations disclosed hereinabove, respectively. In algorithm 1, both steps 1 and 3 involve the matrices A and $A^T$, while step 2 involves matrix B. In the context of the MAP ECT reconstruction, matrix A is a dense matrix of a large size and matrix B is a sparse matrix of a relatively small size. As a result, computation with the matrix A or $A^T$ is more costly than computation with the matrix B. To reduce the overall computational cost, in one instance, the inner iteration is carried out with an appropriate choice of iteration number r. By paying less computational effort with an appropriate r, we could obtain a more accurate estimate $f^{(k+1)}$ at the kth outer iterate.

The preconditioning matrix S is not specified in algorithm 1. The choice of the preconditioning matrix is important in designing computationally efficient algorithms. One may choose the preconditioning matrix S as the identity matrix, which corresponds to the case without preconditioning. More interesting cases are the identity choices. The choice of the preconditioning matrix S may be motivated from different ways with the same purpose of speeding up the convergence of the algorithm. A possible choice is motivated by the idea of the projected Newton method.

One choice of the preconditioner S is inspired by the classical EM algorithm. Recall that EM is an iterative scheme for computing the ML estimate. In the conventional EM algorithm, when the EM algorithm is applied to ECT reconstruction, for any $f^{(0)} \in R^d_+$, $$f^{(k+1)} = E^{(k)} A^T \left(\frac{g}{Af^{(k)} + \gamma}\right)$$

where $E^{(k)}$ is a diagonal matrix defined by $$E^{(k)} := \text{diag}\left(\frac{f^{(k)}}{A^T I}\right)$$

In the EM algorithm, the matrix $E^{(k)}$ determines the direction for the next step of a search for the minimizer, for the purpose of finding the ML estimate. By comparing the expression for $f^{(k+1)}$ in the EM algorithm with the form of $\nabla fH$ given hereinabove, motivated by the matrix $E^{(k)}$ having the form shown hereinabove, in one instance, the matrix S in algorithm 1 is chosen as the diagonal matrix $E^{(k)}$ at the kth iteration. This choice of the preconditioning matrix allows the search of the minimizer to follow the direction of the search in the classical EM algorithm for finding the ML estimate while preserving the advantage of the alternating projection nature in the algorithm of these teachings. In this way, the preconditioning matrix is updated at every iterate step when a new value $f^{(k)}$ is available. This leads to the following algorithm (algorithm 2) for the MAP ECT reconstruction.

Algorithm 2: (Preconditioned alternating projection algorithm for MAP ECT reconstruction)
Preparation: $\nabla fH$, $\nabla bH$ and r are defined hereinabove respectively. The parameter r is a positive integer.
Initialization: $f(0)=1$, $b(0)=0$.
repeat
    Step 1: $S^{(k)} \leftarrow \text{diag}\left(\frac{f^{(k)}}{A^T I}\right)$
    Step 2: $h^{(k)} \leftarrow P^d_R + (f^{(k)} - \tau S^{(k)} \nabla_f H(f^{(k)}, b^{(k)}))$
    Step 3: $b^{(k+1)} \leftarrow Q^r_{h(k)}(b(k))$
    Step 4: $f^{(k+1)} \leftarrow P^d_R + (f^{(k)} - \tau S^{(k)} \nabla fH(f^{(k)}, b^{(k+1)}))$ until 'convergence'

Since the choice of S is motivated from the EM algorithm, algorithm 2 is referred to as the EM PAPA for MAP ECT reconstruction and the matrix E is referred to as the EM-preconditioner. A numerical comparison of the proposed algorithms 1 and 2 will be presented hereinbelow. The numerical study shows that the EM-preconditioner speeds up significantly the convergence of the alternating projection algorithm.

The PAPA which was described hereinabove and in algorithm 1 has a fixed preconditioning matrix S. The preconditioner in algorithm 2 changes dynamically from step to step. Hereinbelow, the dynamics of the EM-preconditioner are analyzed numerically and it is shown that after some iteration steps, the change in the EM-preconditioner is so small that it can be neglected. In other words, the EM-preconditioner tends to a fixed preconditioning matrix as the iteration number increases. Therefore, in practice, the preconditioning matrix may be fixed after some iteration steps, which suggests the following semi-dynamic PAPA (algorithm 3 of these teachings).

Algorithm 3: (Semi-dynamic PAPA for MAP ECT reconstruction)

Preparation: $\nabla_f H$, $\nabla_b H$ and $\tau$ are defined hereinabove respectively. The parameters r and l are positive integers.
Initialization: $f(0)=1$, $b(0)=0$.
Run algorithm 2 until k>1.

$$\text{Set } S^{(l)} = \text{diag}\left(\frac{f^{(l)}}{A^T I}\right)$$

repeat
Step 1: $h^{(k)} \leftarrow P_R^d + (f^{(k)} - \tau S^{(k)} \nabla_f H(f^{(k)}, b^{(k)}))$
Step 2: $b^{(k+1)} \leftarrow Q^Y_{h(k)}(b(k))$
Step 3: $f^{(k+1)} \leftarrow P_R^d + f^{(k)} - \tau S^{(k)} \nabla_f H(f^{(k)}, b^{(k+1)})$
until 'convergence'

Hereinbelow numerical results obtained from computational experiments for the proposed algorithms are presented. The algorithms of these teachings are compared with the conventional EM-TV algorithm (disclosed in Panin V, Zeng G and Gullberg G, Total variation regulated EM algorithm, *IEEE Trans. Nucl. Sci.* 46 2202-10 (1999), which is incorporated by reference herein in its entirety and for all purposes) and the nested EM-TV algorithm (disclosed in Sawatzky A, Brune C, Wubbeling F, Kosters T, Schafers K and Burger M 2008 Accurate EM-TV algorithm in pet with low SNR *Proc. IEEE Nuclear Science Symp. Conf Record* pp 5133-7, which is incorporated by reference herein in its entirety and for all purposes) in terms of the reconstruction quality and computational performance.

Figure 4A:
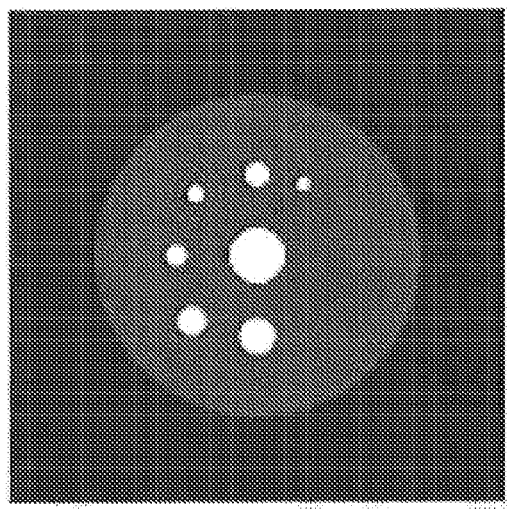
FIGS. 4a-4c show the Morphology of numerical phantom used.
Figure 4B:
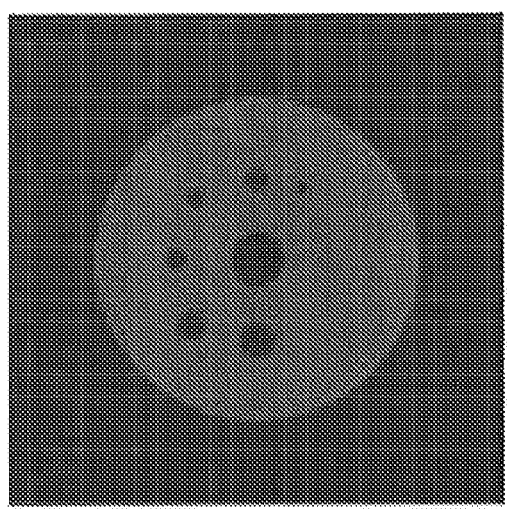
Figure 4C:
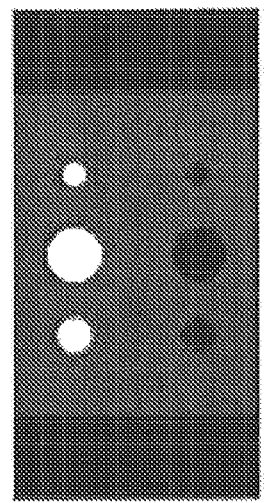
Figure 5B:
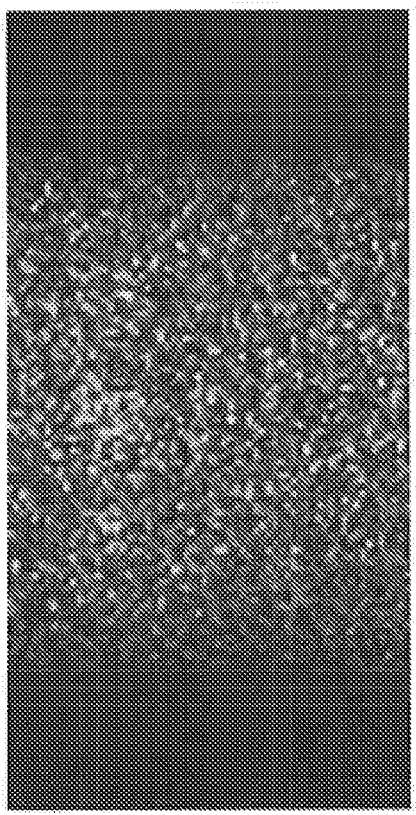
FIG. 5a-5b show an example of one parallel-beam collimator SPECT projection view, out of 120 views in the projection set, simulated for one noise realization for a digital phantom shown in FIG. 1: (a) 15% Poisson noise, $1.62 \times 10^5$ counts per view and (b) 56% Poisson noise, $1.49 \times 10^4$ counts per view.
Figure 5A:
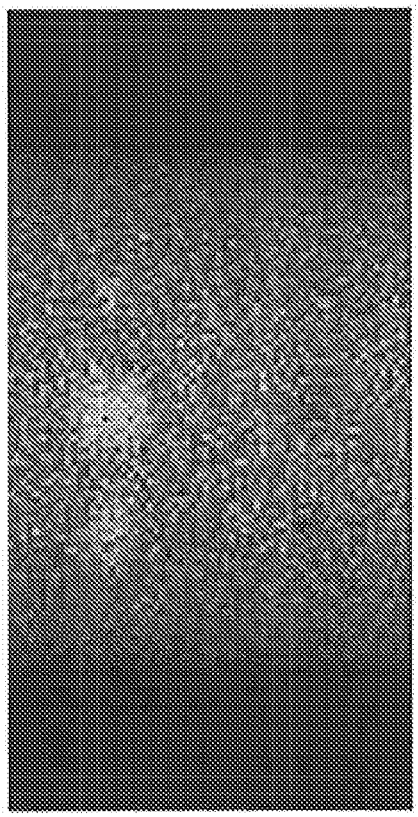
Figures 7A, 7B, 7C, 7D:
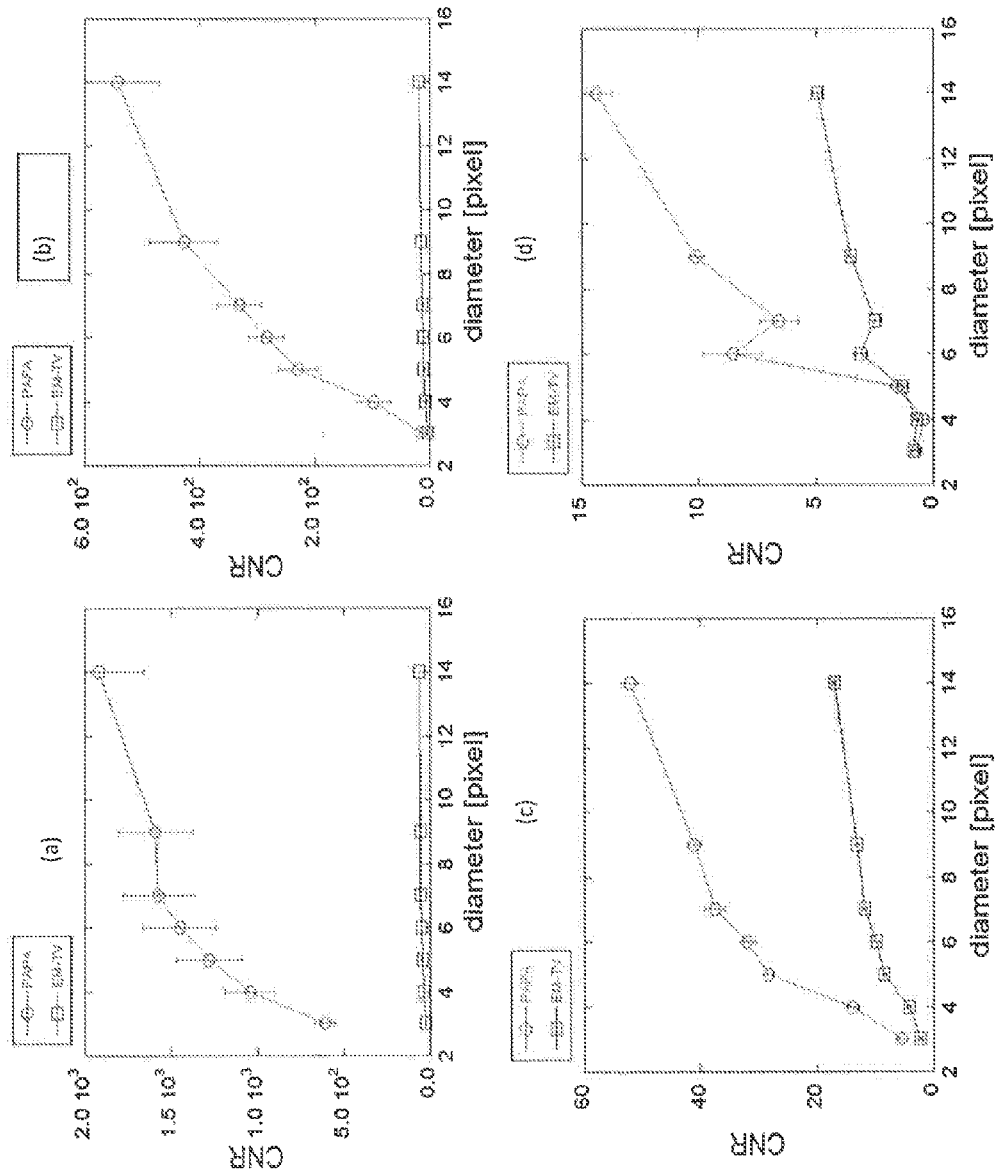
FIGS. 7a-7d show Reconstructed image quality assessment for hot and cold spheres: plots of mean (with respect to five different noise realizations) Contrast-To-Noise (CNR) versus diameter of sphere; the vertical error bars denote the calculated standard deviation of the mean; (a) hot spheres in low-noise phantom, (b) cold spheres in low-noise phantom, (c) hot spheres in high-noise phantom and (d) cold spheres in high-noise phantom; Open circles denote the PAPA.
Figures 8A, 8B, 8C, 8D:
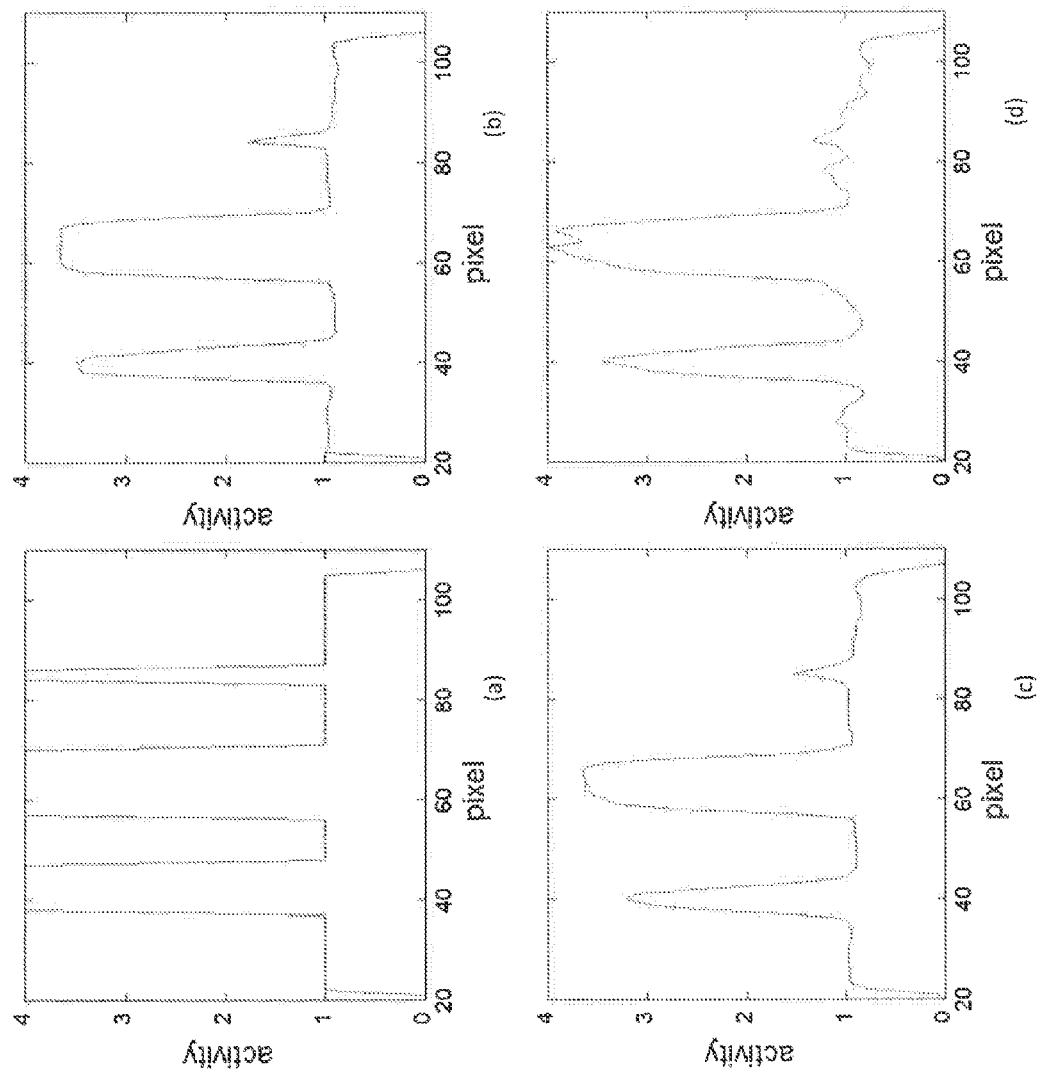
FIGS. 8a-8d show one-pixel wide line profiles through the centers of hot spheres with 7, 14 and 3-pixel radii in transaxial cross-sections (slice 17) of: (a) the high-noise phantom, (b) image reconstructed using the PAPA from the high-noise phantom data, (c) image reconstructed using the nested EM-TV from the high-noise phantom data and (d) image reconstructed using conventional EM-TV from the high-noise phantom data.
Figures 9A, 9B, 9C, 9D:
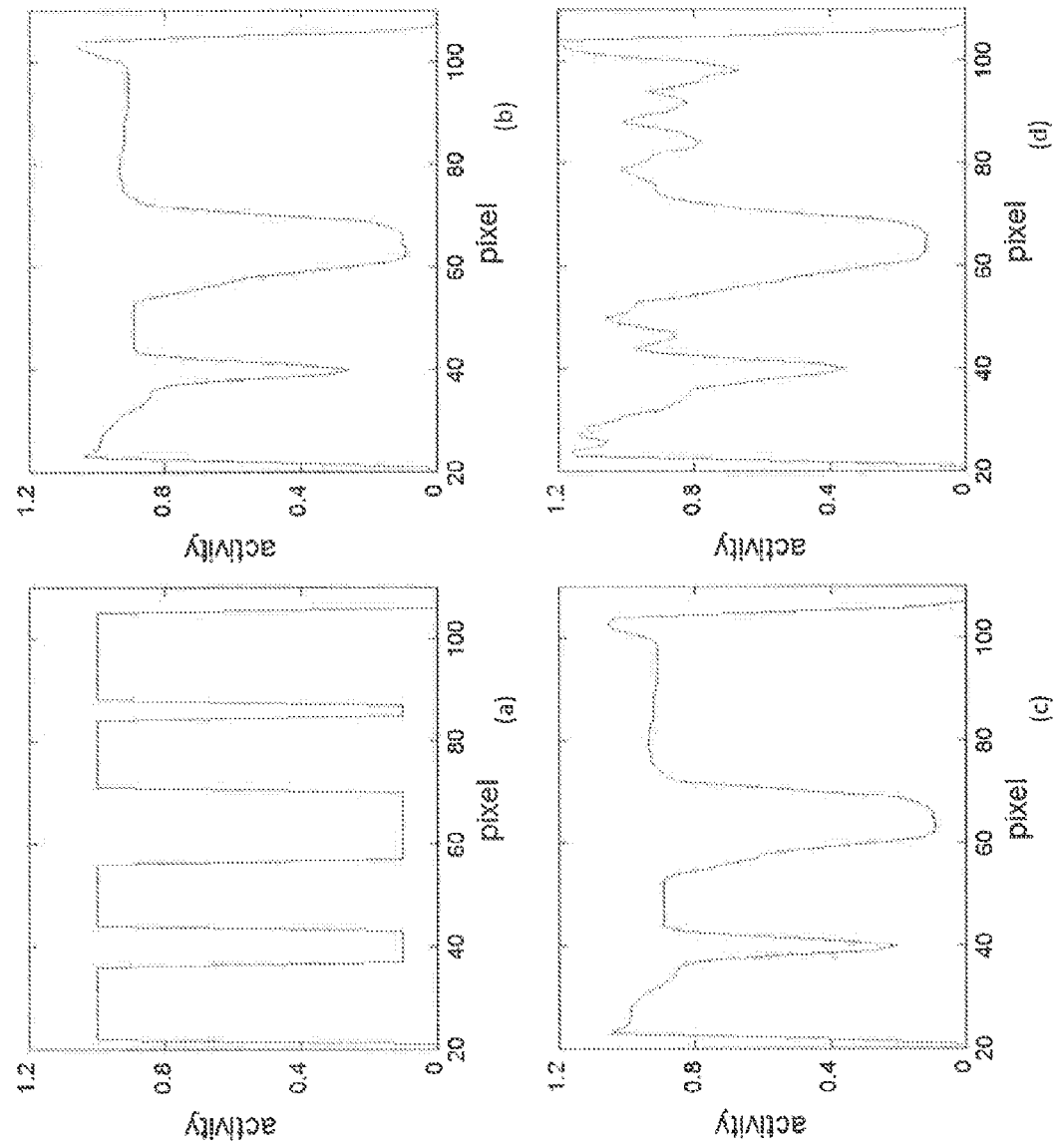
FIGS. 9a-9d show One-pixel wide line profiles through the centers of cold spheres with 7-, 14- and 3-pixel radii in transaxial cross-sections (slice 49) of (a) the high-noise phantom, (b) image reconstructed using the PAPA from the high-noise phantom data, (c) image reconstructed using the nested EM-TV from the high-noise phantom data and (d) image reconstructed using conventional EM-TV from the high-noise phantom data.

A digital cylindrical emission phantom with uniform mean background activity distribution (i.e. with uniform mean number of nuclear disintegrations per time unit and per unit volume) and sets of seven hot spheres and seven cold spheres embedded in the cylinder was constructed. The hot and cold spheres simulate hyperperfused and hypoperfused defects, respectively. Such defects are of interest in nuclear medicine and one of the main tasks of ECT is detection of such defects. Mean activities across all spheres are uniform. The mean activity ratio of hot:background:cold areas is 40:10:1, respectively. The pixel size used is 0.172 cm. The phantom dimensions are: base radius 84 pixels and length 128 pixels. The spheres radii are 3, 4, 5, 6, 7, 9 and 14 pixels. Their centers are in slices 33 and 97. The locations of spheres in transaxial and sagittal planes are shown in FIG. 4. The spheres are separated by a uniform region located between slices 47 and 82. The mean activity distribution in the phantom represents the mean radiotracer distribution, i.e. the image $f$. The parallel-collimator SPECT projection data for our experiments consist of 120 views in 256×128 matrix with pixel size 1.78 mm and were generated using analytical pixel-wise discretized projector A with 20 rays per detector bin. The generated data follow Poisson probability distribution created by a random number generator and the total number of detector counts in 120 views equal to $1.79 \times 10^6$ and $1.947 \times 10^7$ corresponding to approximately 10:1 total activities ratio. Neither attenuation nor scatter was modeled and an ideal detector was assumed. Each image in these projection sets was then downsampled to a 128×64 matrix with the pixel size 3.56 mm. The coefficient of variation (CV) defined as the ratio of the standard deviation to the mean in the projection image of a sufficiently large uniform region away from edges is used as a measure of Poisson noise in the noisy projection data. Using such a definition, our projection sets are characterized at 56% and 15% noise levels, respectively (FIG. 5a-b). For the sake of convenience, the phantom with higher (less noisy) and lower total activity (more noisy) is called 'low-noise phantom' and 'high-noise phantom', respectively. The low-noise phantom corresponds to clinically realistic SPECT data, while the high-noise phantom SPECT data would result in clinically unacceptable high noise in the reconstructed images if treated with the conventional reconstruction techniques. Examples of one noise realization for one projection view are shown in FIG. 5a-b.

Hereinbelow the numerical performance of the algorithms of these teachings: algorithms 1-3 is assessed in image reconstruction for the SPECT projection data generated from the low-noise and high-noise phantoms. Specifically, three issues related to the proposed algorithms: the necessity of the preconditioning, the convergence of the proposed preconditioner and the role of the multiple iteration steps in the inner iteration are considered.

In the numerical experiments, the regularization parameter. in the Poisson-TV model (6) is chosen by adopting the bias-noise curve method. Specifically, bias and the CV in a reconstructed background region of interest for candidate regularization parameters (ranging from $1 \times 10^{-4}$ to 1) were calculated, and obtained the bias-CV curve. When choosing the optimal parameters, the best trade-off between bias and CV was considered. Furthermore, in order to improve the statistical accuracy, three SPECT projection data sets with different noise realizations from the low-noise and the high-noise phantom, respectively, were generated and evaluated the mean values of bias and CV with respect to the three different noise realizations. In particular, in the numerical experiments, the regularization parameter. in the Poisson-TV model (6) is chosen to be 0.1 and 0.2 for the SPECT projection data sets generated from low-noise and high-noise phantom, respectively. The constant γ in the model is set to be 0.01 for both phantoms. Let $\{f^{(k)}: k \in N\}$ be a sequence generated by either algorithm 1, 2 or 3. For a pre-given tolerance tol, the iterative process of an algorithm is terminated if the following requirement is satisfied:

$$\frac{\|f^{(k)} - f^{(k+1)}\|}{\|f^{(k+1)}\|} \leq tol.$$

The parameters in algorithms 1-3 are specified as follows. For algorithm 1, without preconditioning, (S=I) β is chosen to be $10^7$ times of the upper bound given by $$\frac{(1-\varepsilon)\lambda\gamma^2}{2\|g\|_\infty \|S\|_2^2 \|A\|_2^2}$$

(suggested in Theorem 4.7 in A Krol et al, Inverse Problems 28 (2012), which is incorporated by reference herein in its entirety and for all purposes) and $$\mu := \frac{1}{2\beta \|B\|_2^2}.$$

For algorithm 1 with the fixed diagonal preconditioner $$\text{diag}(1/A^T 1),$$

we set $$\beta = \lambda, \text{ and } \mu = \left(2\lambda \|B\|_2^2 \left\|\frac{1}{A^T 1}\right\|_\infty\right)^{-1}.$$

For algorithms 2 and 3, we set $\beta = \lambda$, and $$\mu = \left(2\lambda \|B\|_2^2 \left\|\frac{f^{(k)}}{A^T 1}\right\|_\infty\right)^{-1}$$

in their kth iterations.

In the first experiment, the performance of algorithm 1 without preconditioning (S=I) is compared to that of algorithm 1 with the fixed diagonal preconditioner $$\text{diag}\left(\frac{1}{A^T 1}\right)$$

and that of algorithms 2 and 3. The parameter r for all the algorithms is fixed at 10 and the other parameters for each algorithm are chosen as discussed above. When implementing algorithm 3, in the first 100 iterations, the dynamic preconditioner is used and after 100 iterations, the preconditioner is held fixed. FIG. 5c gives a summary of the CPU times (process times) and numbers of the complete iterations for reconstructing images from the noisy SPECT projection data set generated from low-noise phantom. It clearly shows that algorithms 2 and 3, which have dynamic and semi-dynamic EM-preconditioners, respectively, converge significantly faster than algorithm 1 with either preconditioner. We remark that algorithm 1 with either preconditioner cannot meet the stopping criteria for the last tolerance level. This phenomenon is marked by (−, −) in the table. Therefore, in the remaining part of this section, only algorithm 3 will be used to compare with other existing algorithms for the Poisson-TV model of equation (6). For comparison, the numerical results for the P-PD algorithm which also uses a fixed preconditioner are included in FIG. 5c. The performance of the P-PD algorithm is even worse than that of algorithm 1 with the fixed diagonal preconditioner $$\text{diag}\left(\frac{1}{A^T 1}\right).$$

The preconditioner disclosed hereinabove depends on the current iterate and is updated at each iterate step. The second experiment explores numerically how the preconditioner $$\text{diag}\left(\frac{f^{(k)}}{A^T 1}\right)$$

changes in iterations in terms of its $\ell^2$-norm and Frobenius norm. FIGS. 6a-b presents the curves of both norms versus iteration numbers for the low-noise and high-noise phantoms. From the figure, it can be concluded that after a few iterations, the change of the preconditioner is negligible. This suggests that except for the first few iterations, the preconditioner may be chosen to be the same. In this regard, the convergence result that was established for the fixed preconditioner is applicable to the practical situation.

The third experiment tests numerically the choice of the parameter r in the inner iteration for algorithm 3 (PAPA) in terms of the CPU time that the algorithm requires to reach the stopping criterion (61) for different tolerances. The PAPA is exercise with r from 6 to 15 for the noisy SPECT projection data sets generated from low-noise and high-noise phantoms with the tolerance tol=10-6. The numerical results for the noisy SPECT projection data set generated from the low-noise phantom show that the algorithms with the parameter r ranging from 7 to 11 perform comparably and are better than those with other ranges of r. The numerical results for the noisy SPECT projection data set generated from the high-noise phantom indicate that the algorithms with the parameter r ranging from 10 to 12 perform comparably and are better than those with other ranges of r. According to this numerical observation, in the remaining part of this section, we fix the parameter r for the PAPA at 10

$$\text{diag}\left(\frac{1}{A^T 1}\right)$$

We now compare performance of the proposed PAPA with that of the conventional EM-TV [48], in terms of the CPU time, local image quality metrics: the CV measured within the uniform region of interest, contrast-to-noise ratio (CNR) and a global image quality metric, i.e. the normalized mean-squared error (NMSE).

For reconstructions with the conventional EM-TV algorithm, following Panin V, Zeng G and Gullberg G, Total variation regulated EM algorithm, *IEEE Trans. Nucl. Sci.* 46 2202-10 (1999), $\delta=0.001$ is used which is less than 1% of the maximum value of the phantom. Moreover, it should be noted that when $\lambda$ vanishes the conventional EM-TV algorithm reduces to the EM algorithm.

The quality of the reconstructed images was of value. First, noise in the reconstructed images was compare. The CV within a uniform region of interest was used as a surrogate of noise measure in the reconstructed images obtained using algorithm 2 and the conventional EM-TV. The CV of an image $f$ reconstructed by an algorithm is defined by $$CV := \frac{SD_\Omega(f^\infty)}{E_\Omega(f^\infty)}$$

where $SD_\Omega(\bullet)$ and $E_\Omega(\bullet)$ denote the standard deviation and the mean of the reconstructed activities over a region $\Omega$. In our case, the region $\Omega$ is a cylinder with the radius of base and the height equal to 25 and 8 pixels, respectively. This cylindrical region lies between the hot spheres and the cold spheres (refer to FIG. 1(c)) and does not intersect with any hot or cold spheres. Under these circumstances, the means of CVs (with respect to five different noise realizations) for the PAPA and the conventional EM-TV are 0.12% and 3.81%, respectively, for the low-noise phantom, and are 4.09% and 13.15%, respectively, for the high-noise phantom. From these numerical results, we find out that the PAPA performs considerably (factor of 31 for low-noise phantom data and factor of 3 for high-noise phantom data) better than the conventional EM-TV in terms of the noise.

Next, a local quality metric, CNR, of images will be used to measure the quality of the reconstructed hot or cold spheres. Too low CNR might result in inability to detect the lesion by an observer. The CNR for a reconstructed image $f^\infty$ is defined as a ratio of a lesion contrast to the background noise $$CNR := \frac{|E_{\Omega T}(f^\infty) - E_{\Omega B}(f^\infty)|}{SD_{\Omega B}(f^\infty)}$$

Here, $En_{\Omega T}(f^\infty)$ is the mean reconstructed activity in the region $\Omega_T$ where a specific hot (resp. cold) sphere is located, while $\Omega_B$ is a spherical region with the same diameter as the hot (resp. cold) sphere but located within the uniform region of the cylindrical phantom that does not intersect with any hot or cold sphere. The CNR metric is important in radiology because it allows one to assess detectability of a lesion that is one of the main tasks of ECT. It is well established by human observer studies that the lesion contrast and the background noise influence lesion detectability. It should be noted that even when the signal-to-noise ratio is high, the presence of a significant bias in the reconstructed image might result in the lesion contrast being too low for a lesion to be detected. Very high noise or correlation of the noise will contribute to low detectability of the lesion even if the lesion contrast is high. The curves of the means of CNRs (with respect to five different noise realizations again) versus diameters of spheres are plotted in FIGS. 7a-d. Again, it is observed that the PAPA significantly (factor of 7-14 for high-noise phantom) outperforms the conventional EM-TV in terms of the CNR values.

The NMSE is used to assess accuracy of reconstructions. The NMSE is a global image quality metric. It quantifies the difference between the activity reconstruction $f^\infty$ and the true mean activity $f$ in the whole object. It is defined by $$NMSE := \frac{\|f - f^\infty\|}{\|f\|^2}$$

The mean values of NMSE (with respect to five different noise realizations) for the images reconstructed by the PAPA and the conventional EM-TV are 0.485 and 0.787, respectively, for the low-noise phantom, and 2.55 and 3.93, respectively, for the high-noise phantom. Once again, the PAPA significantly outperforms the conventional EM-TV in terms of the NMSE values.

The performance of the PAPA of these teachings has been compared with that of the nested EM-TV algorithm, the algorithm recently described in Sawatzky A, Brune C, Wubbeling F, Kosters T, Schafers K and Burger M, (2008) Accurate EM-TV algorithm in pet with low SNR, *Proc. IEEE Nuclear Science Symp. Conf Record*, pp 5133-7.

This algorithm has two major steps, i.e. the EM step and the TV correction step, and they are performed alternatively. The EM step is conventional. The TV correction step is a modified version of the Rudin-Osher-Fatemi (ROF) model and was implemented by exploiting an existing scheme for the ROF model. It is stated in Sawatzky A, Brune C, Wubbeling F, Kosters T, Schafers K and Burger M, (2008) Accurate EM-TV algorithm in pet with low SNR, *Proc. IEEE Nuclear Science Symp. Conf Record*, pp 5133-7 that the correction step was carried out by adopting Chambolle's method. The suggestion made in Sawatzky et al. to apply Chambolle's method with ten iterations for each TV correction step to achieve an approximate solution was followed.

In Table 1, the CPU time expended and the number of the complete iterations used by the PAPA, the nested EM-TV and the conventional EM-TV are given for the two SPECT projection data sets. After examining the table, it can be concluded that under the same stopping criteria the PAPA of these teachings is better than the nested EM-TV and significantly better than the conventional EM-TV in terms of the convergence speed. It can be remarked that the conventional EM-TV algorithm cannot meet the stopping criteria for most of the given tolerance levels.

In addition to the CPU time and the number of complete iterations, the number of arithmetic operations for the PAPA and the nested EM-TV algorithm are estimated. Table 2 shows the number of total arithmetic operations required by the PAPA and the nested EM-TV, under various stopping criteria.

The image quality metrics of the reconstructed images obtained by using the PAPA and by the nested EM-TV was compared. The means of CVs for the reconstructions by the PAPA and the conventional EM-TV are reported in Table 3. The means of CNRs with respect to five different noise realizations versus the diameters of the hot spheres (resp. cold spheres) for the PAPA, the nested EM-TV and the conventional EM-TV are listed in Table 4 (resp. 6). Moreover, the means of NMSEs with respect to 5 different noise realizations for the images of the low-noise phantom and the high-noise phantom are presented in Table 5. It can be concluded from these tables that both the PAPA of these teachings and the nested EM-TV outperform the conventional EM-TV in terms of the values of CV, CNR and NMSE, while the PAPA of these teachings performs comparably with the nested EM-TV.

Based on the numerical experiments performed in this work, it is observed that the alternating projection algorithm of these teachings with the EM-preconditioner significantly outperforms the conventional EM-TV algorithm in all aspects including the convergence speed, the noise in the reconstructed images and the image quality. It also outperforms the recently developed algorithm—the nested EM-TV—in the convergence speed while having a comparable image quality.

The alternating projection algorithms of these teachings with dynamic or semi-dynamic EM-preconditioner could allow very significant reduction in the radiation dose to the patients imaged using ECT by providing the same CNR for hot and cold lesions as the conventional EM-TV algorithm, but with the total administered radiotracer activity two to six times lower than presently used in ECT examinations reconstructed using the conventional EM-TV algorithm.

TABLE 1

Comparison of arithmetic operations of semi-dynamic PAPA and the nested EM-TV for the test data. The number (·) represents (·) × $2^{20}$ arithmetic operations required.

| Algorithm | tol | | | | | | |
|---|---|---|---|---|---|---|---|
| | $10^{-1}$ | $10^{-2}$ | $10^{-3}$ | $10^{-4}$ | $10^{-5}$ | $10^{-6}$ | $10^{-7}$ |
| Low-noise phantom | | | | | | | |
| PAPA | 3380 | 9464 | 29 744 | 83 148 | 207 532 | 400 192 | 1080 924 |
| Nested EM-TV | 3795 | 10 626 | 32 637 | 88 803 | 233 013 | 589 743 | 1653 861 |
| High-noise phantom | | | | | | | |
| PAPA | 3380 | 9464 | 28 392 | 79 092 | 195 364 | 392 080 | 1176 916 |
| Nested EM-TV | 3795 | 10 626 | 31 878 | 84 249 | 220 869 | 559 383 | 1552 155 |

TABLE 2

Means of CVs for the reconstructions by the PAPA, the nested EM-TV and the conventional EM-TV.

| Phantom | Low-noise phantom | High-noise phantom |
|---|---|---|
| PAPA | 0.12% | 4.09% |
| Nested EM-TV | 0.14% | 4.54% |
| EM-TV | 3.81% | 13.15% |

TABLE 5

Means of NMSEs for the reconstructions by the PAPA, the nested EM-TV and the conventional EM-TV.

| Phantom | Low-noise phantom | High-noise |
|---|---|---|
| PAPA | 0.48469 | 2.54701 |
| Nested EM- | 0.48481 | 2.54794 |
| EM-TV | 0.78670 | 3.92571 |

TABLE 3

Means of CNRs for seven hot spheres reconstructed using the PAPA, the nested EM-TV and the conventional EM-TV.

| | Diameters of spheres | | | | | | |
|---|---|---|---|---|---|---|---|
| | 14 | 9 | 7 | 6 | 5 | 4 | 3 |
| Low-noise phantom | | | | | | | |
| PAPA | 1915.768 | 1590.557 | 1574.134 | 1451.297 | 1280.732 | 1043.835 | 611.271 |
| Nested EM-TV | 1912.141 | 1587.496 | 1571.388 | 1448.454 | 1277.969 | 1041.962 | 610.677 |
| EM-TV | 65.801 | 55.159 | 56.717 | 51.872 | 47.284 | 40.451 | 28.124 |
| High-noise phantom | | | | | | | |
| PAPA | 52.171 | 41.019 | 37.525 | 31.919 | 28.247 | 13.939 | 5.448 |
| Nested EM-TV | 52.149 | 41.002 | 37.510 | 31.905 | 28.234 | 13.932 | 5.445 |
| EM-TV | 17.007 | 13.116 | 11.885 | 9.815 | 8.389 | 4.237 | 2.232 |

TABLE 4

Means of CNRs for seven cold spheres reconstructed using the PAPA, the nested EM-TV and the conventional EM-TV.

| | Diameters of spheres | | | | | | |
|---|---|---|---|---|---|---|---|
| | 14 | 9 | 7 | 6 | 5 | 4 | 3 |
| Low-noise phantom | | | | | | | |
| PAPA | 543.563 | 427.444 | 330.512 | 283.982 | 229.776 | 97.887 | 14.505 |
| Nested EM-TV | 542.524 | 426.538 | 330.087 | 283.587 | 229.380 | 97.331 | 14.437 |
| EM-TV | 18.721 | 15.195 | 12.599 | 11.744 | 10.610 | 6.785 | 3.993 |
| High-noise phantom | | | | | | | |
| PAPA | 14.378 | 10.106 | 6.577 | 8.570 | 1.543 | 0.424 | 0.764 |
| Nested EM-TV | 14.373 | 10.105 | 6.576 | 8.568 | 1.542 | 0.424 | 0.762 |
| EM-TV | 4.929 | 3.544 | 2.484 | 3.128 | 1.310 | 0.724 | 0.839 |

To better access the differences between images reconstructed using the PAPA and the nested EM-TV, line profiles were obtained through selected transaxial cross-sections of the reconstructed images containing the hot and cold spheres. They are shown in FIGS. 8a-d and 9a-d for hot and cold spheres, respectively. It is observed that for hot spheres reconstructions PAPA provides images with slightly better contrast and spatial resolution, as compared to the nested EM-TV. For cold spheres reconstructions both algorithms perform similarly. The conventional EM-TV reconstructions are inferior in any case.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off. Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although these teachings has been described with respect to various embodiments, it should be realized these teachings is also capable of a wide variety of further and other embodiments within the spirit and scope of the claims.

What is claimed is:

1. A method, implemented utilizing a computer, for obtaining a reconstruction of an object from data, the reconstruction of the object comprising an inverse problems, the method comprising:
   expressing the reconstruction of the object as an optimization problem with total variation regularization; the object being an input to a system, the system providing output data resulting from the input, the object being reconstructed from the output data obtained from interaction of the object with the system; the system comprising a medical imaging system;
   expressing a solution of the optimization problem as a system of fixed point equations, each of the fixed point equations expressed using projections; wherein at least some of the projections are expressed using proximity operators;
   performing iterations applying the projections alternatingly; and
   obtaining the reconstruction of the object from convergence of the iterations;
   iterations being performed by means of a computer usable medium having computer readable code that causes the computer to perform the iterations;
   wherein, for data from emission computed tomography (ECT) obtained with a reduced radiation dose, two to six times lower than presently used, a reconstruction of the object is obtained.

2. The method of claim 1 wherein the reconstruction of the object is expressed as $$\min\{<Af,1>-<\ln(Af+\gamma),g>+\lambda(\phi \circ B)(f): f \in Rd\}.$$

where g is the output data resulting from the input,
$f$ is the object,
A is the operator representing the system,
$\gamma$ is the background noise,
$\lambda$ is a regularization parameter, and
$(\phi \circ B)(f)$ is a total variation regularization expression;
and wherein the fixed point equations are $$b=(I-\text{prox}_{\mu^{-1}\phi})(b+\sigma \nabla_b H(f,b)),$$

$$f=\text{prox}_\gamma(f-\tau S \nabla_f H(f,b)).$$

where I is the identity matrix or operator,
prox is the proximity
operator, $\nabla$ is the gradient operator with respect to the subscripted variable,
$f \in Rd$ denotes that $f$ is a d-dimensional vector in a space of reals; and $$H=<Af,1>-<\ln(Af+\gamma),g>+\lambda(\phi \circ B)(f): f \in Rd$$

where $\lambda$, $\beta$ and $\mu$ are positive numbers, $$\tau := \frac{\beta}{\lambda}, \sigma := \frac{1}{\lambda\mu}$$

and S is a predetermined matrix including an identity matrix.

3. The method of claim 2 wherein S is a preconditioner.

4. The method of claim 3 wherein the preconditioner in one iteration is different from the preconditioner in a subsequent iteration.

5. The method of claim 1 further comprising using a preconditioner in one of the fixed point equations using projections in order to improve convergence while not substantially affecting result of the convergence.

6. The method of claim 1 wherein the object is an image from emission computed tomography (ECT), output data is scanner projection data; the system being expressed as:

$$g=Af+\gamma$$

where g are expected photon counts, A is a system matrix, $f$ is an expected radiotracer distribution, $\gamma$ is background photon count.

7. The method of claim 6 wherein reconstruction of the expected radiotracer distribution is expressed as:

$$\min\{<Af,1>-<\ln(Af+\gamma),g>+\lambda(\phi\bigcirc B)(f):f\in Rd\}.$$

where $\lambda$ is a regularization parameter, and
$(\phi\bigcirc B)(f)$ is a total variation regularization expression;
and wherein the fixed point equations are $$b=(l-\text{prox}_\mu{}^{-1}{}_\phi)(b+\sigma\nabla_b H(f,b)),$$

$$f=\text{prox}_\gamma(f-\tau S\nabla_f H(f,b)),$$

where l is the identity matrix or operator,
prox is the proximity operator,
$\nabla$ is the gradient operator with respect to the subscripted variable,
$f\in Rd$ denotes that $f$ is a d-dimensional vector in a space of reals; and $$H=<Af,1>-<\ln(Af+\gamma),g>+\lambda(\phi\circ B)(f):f\in Rd$$

where $\lambda$, $\beta$ and $\mu$ are positive numbers, $$\tau := \frac{\beta}{\lambda},\ \sigma := \frac{1}{\lambda\mu}$$

and S is a predetermined matrix including an identity matrix.

8. The method of claim 7 wherein S is a preconditioner.

9. The method of claim 8 wherein S is given by $$\text{diag}\left(\frac{f^k}{A^T 1}\right)$$

where diag indicates a diagonal matrix, $A^T$ is a transpose of the system matrix, I is a unitary matrix and k indicates a kth iteration.

10. A system comprising:
at least one processor; and
at least one computer usable medium having computer readable code embodied therein, said computer readable code causing said at least one processor to:
receive data from interaction of an object with a data providing system; wherein the object is an input to the data providing system, the data providing system provides output data resulting from the input, the object is reconstructed from the output data obtained from interaction of the object with the data providing system; the data providing system comprising a medical imaging system;
express the reconstruction of the object as an optimization problem with total variation regularization;
express a solution of the optimization problem as a system of fixed point equations, each of the fixed point equations expressed using projections, wherein at least some of the projections are expressed using proximity operators;
perform iterations applying the projections alternatingly; and
obtain the reconstruction of the object from convergence of the iterations;
wherein, for data from emission computed tomography (ECT) obtained with a reduced radiation dose, two to six times lower than presently used, a reconstruction of the object is obtained.

11. The system of claim 10 wherein the reconstruction of the object is expressed as $$\min\{<Af,1>-<\ln(Af+\gamma),g>+\lambda(\phi\circ B)(f):f\in Rd\}.$$

where g is the output data resulting from the input,
$f$ is the object,
A is the operator representing the system,
$\gamma$ is the background noise,
$\lambda$ is a regularization parameter, and
$(\phi\circ B)(f)$ is a total variation regularization expression;
and wherein the fixed point equations are $$b=(l-\text{prox}_\mu{}^{-1}{}_\phi)(b+\sigma\nabla_b H(f,b)),$$

$$f=\text{prox}_\gamma(f-\tau S\nabla_f H(f,b)),$$

where l is the identity matrix or operator,
prox is the proximity operator,
$\nabla$ is the gradient operator with respect to the subscripted variable,
$f\in Rd$ denotes that $f$ is a d-dimensional vector in a space of reals; and $$H=<Af,1>-<\ln(Af+\gamma),g>+\lambda(\phi\circ B)(f):f\in Rd$$

where $\lambda$, $\beta$ and $\mu$ are positive numbers, $$\tau := \frac{\beta}{\lambda},\ \sigma := \frac{1}{\lambda\mu}$$

and S is a predetermined matrix including an identity matrix.

12. The system of claim 11 wherein S is a preconditioner.

13. The system of claim 12 wherein the preconditioner in one iteration is different from the preconditioner in a subsequent iteration.

14. The system of claim 10 wherein said computer readable code is also capable of causing said at least one processor to use a preconditioner in one of the fixed point equations in order to improve convergence while not substantially affecting result of the convergence.

15. The system of claim 10 wherein the object is an image from emission computed tomography (ECT), output data is scanner projection data; the system being expressed as:

$$g=Af+\gamma$$

where g are expected photon counts, A is a system matrix, $f$ is an expected radiotracer distribution, $\gamma$ is background photon count.

16. The system of claim 15 wherein reconstruction of the expected radiotracer distribution is expressed as:

$$\min\{<Af,1>-<\ln(Af+\gamma),g>+\lambda(\phi\circ B)(f):f\in Rd\}.$$

where
$\lambda$ is a regularization parameter, and
$(\phi\circ B)(f)$ is a total variation regularization expression;
and wherein the fixed point equations are $$b=(l-\text{prox}_\mu{}^{-1}{}_\phi)(b+\sigma\nabla_b H(f,b)),$$

$$f=\text{prox}_\gamma(f-\tau S\nabla_f H(f,b)).$$

where l is the identity matrix or operator,
prox is the proximity
operator, $\nabla$ is the gradient operator with respect to the subscripted variable, $f \epsilon Rd$ denotes that $f$ is a d-dimensional vector in a space of reals; and $$H=<Af,1>-<\ln(Af+\gamma),g>+\lambda(\phi \circ B)(f):f \epsilon Rd$$

where $\lambda$, $\beta$ and $\mu$ are positive numbers, $$\tau := \frac{\beta}{\lambda}, \sigma := \frac{1}{\lambda \mu}$$

and S is a predetermined matrix including an identity matrix.

17. The system of claim 16 wherein S is a preconditioner.

18. The system of claim 17 wherein S is given by $$\text{diag}\left(\frac{f^k}{A^T 1}\right)$$

where diag indicates a diagonal matrix, $A^T$ is a transpose of the system matrix, I is a unitary matrix and k indicates a kth iteration.

19. A computer program product comprising:
a non-transitory computer usable medium having computer readable code embodied therein, said computer readable code causing at least one processor to:
receive data from interaction of an object with a data providing system; wherein the object is an input to the data providing system, the data providing system provides output data resulting from the input, the object is reconstructed from the output data obtained from interaction of the object with the data providing system; the data providing system comprising a medical imaging system;
express the reconstruction of the object as an optimization problem with total variation regularization;
express solution of the optimization problem as a system of fixed point equations, each of the fixed point equations expressed using projections;
perform iterations applying the projections alternatingly; and
obtain the reconstruction of the object from convergence of the iterations;
wherein, for data from emission computed tomography (ECT) obtained with a reduced radiation dose, two to six times lower than presently used, a reconstruction of the object is obtained.

20. The computer program product of claim 19 wherein at least some of the projections are expressed using proximity operators.

21. The computer program product of claim 19 wherein the reconstruction of the object is expressed as $$\min\{<Af,1>-<\ln(Af+\gamma),g>+\lambda(\phi \circ B)(f):f \epsilon Rd\}.$$

where g is the output data resulting from the input,
$f$ is the object,
A is the operator representing the system,
$\gamma$ is the background noise,
$\lambda$ is a regularization parameter, and
$(\phi \circ B)(f)$ is a total variation regularization expression;
and wherein the fixed point equations are $$b = (l - \text{prox}_{\mu^{-1}\phi})(b + \sigma \nabla_b H(f,b)),$$

$$f = \text{prox}_\gamma(f - \tau S \nabla_f H(f,b)),$$

where l is the identity matrix or operator,
prox is the proximity
operator, $\nabla$ is the gradient operator with respect to the subscripted variable,
$f \epsilon Rd$ denotes that $f$ is a d-dimensional vector in a space of reals;

$$H=<Af,1>-<\ln(Af+\gamma),g>+\lambda(\phi \circ B)(f):f \epsilon Rd$$

where $\lambda$, $\beta$ and $\mu$ are positive numbers, $$\tau := \frac{\beta}{\lambda}, \sigma := \frac{1}{\lambda \mu}$$

and S is a predetermined matrix including the identity matrix.

22. The computer program product of claim 19 wherein the computer readable code also causes the at least one processor to use a preconditioner in one of the fixed point equations using projections in order to improve convergence while not substantially affecting result of the convergence.

23. The computer program product of claim 19 wherein S is a preconditioner, the preconditioner improving convergence while not substantially affecting result of the convergence.

* * * * *